(12) United States Patent
Jiang et al.

(10) Patent No.: US 9,056,305 B2
(45) Date of Patent: Jun. 16, 2015

(54) CATALYST FOR PREPARING VINYL CHLORIDE, METHODS OF PREPARATION AND APPLICATION THEREOF

(75) Inventors: Biao Jiang, Shanghai (CN); Jinguang Zhong, Xiamen (CN)

(73) Assignees: SHANGHAI CAS ADVANCED RESEARCH INSTITUTE, Shanghai (CN); ZHONGKE YIGONG (XIAMEN) CHEMICAL TECHNOLOGY CO., LTD., Xiamen, Fujian (CN)

( * ) Notice: Subject to any disclaimer, the term of this patent is extended or adjusted under 35 U.S.C. 154(b) by 0 days.

(21) Appl. No.: 13/806,726

(22) PCT Filed: Oct. 26, 2011

(86) PCT No.: PCT/CN2011/081317
§ 371 (c)(1),
(2), (4) Date: Apr. 28, 2013

(87) PCT Pub. No.: WO2013/059998
PCT Pub. Date: May 2, 2013

(65) Prior Publication Data
US 2013/0204052 A1    Aug. 8, 2013

(51) Int. Cl.
| | | |
|---|---|---|
| *B01J 37/34* | (2006.01) | |
| *B01J 21/18* | (2006.01) | |
| *B01J 23/02* | (2006.01) | |
| *B01J 23/06* | (2006.01) | |
| *B01J 27/00* | (2006.01) | |
| *C07C 17/25* | (2006.01) | |
| *C07C 21/00* | (2006.01) | |
| *C07C 21/02* | (2006.01) | |
| *B01J 27/18* | (2006.01) | |
| *C07C 17/08* | (2006.01) | |
| *B01J 37/02* | (2006.01) | |
| *B01J 37/08* | (2006.01) | |
| *B01J 27/138* | (2006.01) | |
| *B01J 37/00* | (2006.01) | |

(52) U.S. Cl.
CPC ............. *B01J 27/1806* (2013.01); *C07C 17/08* (2013.01); *C07C 17/25* (2013.01); *B01J 37/0223* (2013.01); *B01J 37/084* (2013.01); *B01J 21/18* (2013.01); *B01J 27/138* (2013.01); *B01J 37/0018* (2013.01); *B01J 37/0201* (2013.01)

(58) Field of Classification Search
USPC ............................... 502/5, 183, 208; 570/227
IPC ............ B01J 21/18,23/02, 27/08, 27/16, 37/00, B01J 37/0203, 37/08, 37/084; C07C 17/25, C07C 21/00, 21/02, 21/06
See application file for complete search history.

(56) References Cited

U.S. PATENT DOCUMENTS

| | | | | |
|---|---|---|---|---|
| 2,681,372 | A | * | 6/1954 | Trotter ........................ 570/226 |
| 2,750,410 | A | * | 6/1956 | Hanszen et al. ............. 560/242 |
| 2,779,804 | A | * | 1/1957 | Braconier et al. ........... 570/219 |
| 2,830,102 | A | * | 4/1958 | Kobe et al. .................. 570/219 |

FOREIGN PATENT DOCUMENTS

| | | | | | |
|---|---|---|---|---|---|
| CN | 10/1817723 | A | * | 9/2010 | ............ C07C 21/06 |
| CN | 10-2151578 | A | * | 8/2011 | ............ B01J 27/185 |
| CN | 10-2151581 | | * | 8/2011 | |
| CN | 102151581 | A | | 8/2011 | |
| CN | 10-2441407 | A | * | 5/2012 | ............ B01J 27/18 |
| CN | 10-2911007 | A | * | 2/2013 | ............ C07C 21/06 |
| WO | 2013/059998 | | * | 5/2013 | ............ B01J 27/18 |
| WO | 2013/185400 | | * | 12/2013 | ............ C07C 17/08 |

\* cited by examiner

Primary Examiner — Patricia L Hailey
(74) Attorney, Agent, or Firm — Novick, Kim & Lee, PLLC; Allen Xue

(57) ABSTRACT

The present invention discloses a catalyst used in preparing vinyl chloride, its method of preparation, and its applications. Said catalyst used in making vinyl chloride comprises activated carbon as a support, a barium compound and a phosphorus compound supported thereon. The barium compound accounts for 0.2% to 20% of the total mass of the catalyst and the phosphorus compound accounts for 0% to 10% of the total mass of the catalyst based on the mass percentage. A water-soluble barium compound, a water-soluble phosphorus compound, an aqueous polymer monomer, and water are mixed to form a solution or emulsion A. The activated carbon is added into the solution or emulsion A. The activated carbon is removed from water after impregnation, spin-dried, and then the monomers are polymerized. The activated carbon, after polymerization step, is heated to remove water and to decompose and carbonize the polymer. The catalyst after carbonization was activated to obtain a catalyst used in making vinyl chloride.

11 Claims, No Drawings

CATALYST FOR PREPARING VINYL CHLORIDE, METHODS OF PREPARATION AND APPLICATION THEREOF

TECHNICAL FIELD

The present invention relates to a type of catalyst, particularly the type that is used in making vinyl chloride from acetylene dichloroethane and preparation methods thereof.

BACKGROUND

Polyvinyl chloride (PVC) is one of the top five common plastics, widely used in industrial and agricultural production as well as in daily life.

Currently there are two main methods of making PVC: one is the acetylene route, which employs acetylene as the raw material, whose reaction with hydrogen chloride catalyzed by mercuric chloride forms vinyl chloride monomer. This method uses mercuric chloride as a catalyst, which presents the problem of mercury pollution, and largely have been rendered obsolete in foreign countries. The other method is the ethylene route, in which dichloroethane is obtained by direct chlorination of ethylene and oxychlorination. Dichloroethane is converted to vinyl chloride monomer by thermal cracking. This process is widely used in foreign countries.

Since our country has a scarcity of ethylene but is relatively abundant in calcium carbide resources, the PVC production is still mainly based on the calcium carbide route (acetylene produced using calcium carbide), which exerts an enormous strain on environmental protection. Therefore, researchers have been using unremitting efforts to find a catalyst to replace the mercuric chloride catalyst. It is known that compounds having copper, tin, bismuth, lanthanum, barium, cadmium, palladium, gold, or platinum can catalyze the chlorination reaction of acetylene using hydrogen chloride, but the cost of palladium, gold, platinum and other precious metals are too high, while the catalytic effect of the compounds containing copper, tin, bismuth, lanthanum, or barium, etc., are not as good as that of mercuric chloride. Therefore, the mercuric chloride catalyst has not been replaced.

Chinese invention patent application number 2010101492109 disclosed a method for making vinyl chloride using acetylene and ammonium chloride, which uses barium chloride or lanthanum chloride as the catalyst, with a certain degree of success.

Chinese invention patent application number 2010101491801 disclosed a method of making vinyl chloride through acetylene dichloroethane catalytic reforming. This method uses carbon-supported barium chloride as the catalyst and produces vinyl chloride through acetylene dichloroethane catalytic reforming, which achieved good results.

However, it is noticed in simulated industrial operations that catalysts obtained through regular impregnation method have large crystals with an uneven size distribution. The catalyst has poor adhesion with the substrate and is easy to fall off. The catalytic effect and catalyst stability cannot satisfy the requirements for industrial applications.

Therefore, there is an urgent need to provide a catalyst for vinyl chloride preparation that meets the requirements on catalyst activity and stability for industrial operations.

SUMMARY OF INVENTION

The present invention discloses a catalyst for making vinyl chloride and its method of preparation.

In a first aspect of the present invention, there is provided a catalyst for making vinyl chloride. The catalyst uses activated carbon as the carrier, which supports a barium compound and a phosphorus compound on it. Based on the total mass of the catalyst, said barium compound has a mass percentage of 0.2% to 20% and said phosphorus compound has a mass percentage from 0% to 10%. Preferably, said barium compound is barium chloride and said phosphorus compound is phosphoric acid.

In a second aspect of the present invention, there is provided a method of making the catalyst for vinyl chloride production. Said method comprises the steps of:

(1) mixing a water-soluble barium compound, a water-soluble phosphorus compound, an aqueous polymer monomer, and water to obtained a solution A or an emulsion A;

(2) immersing the activated carbon in the solution A or the emulsion A;

(3) spin-drying the impregnated activated carbon and polymerizing the aqueous polymer monomer;

(4) heating the activated carbon to carbonize the polymer; and (5) activating the activated carbon and the substances supported thereon after carbonization to obtain a catalyst for making vinyl chloride of this invention.

In another preferred embodiment, in step (1), said water-soluble barium compound is barium chloride, which has a concentration of 0.3 to 30% in the aqueous solution; said water-soluble phosphorus compound is phosphoric acid, which has a concentration of 0 to 10% in the aqueous solution; in step (1), the aqueous polymer monomer is a compound that is capable of polymerizing into a gel that is soluble or can form an emulsion in water, wherein the compound is chosen from at least one among acrylic compounds, vinyl ester compounds, acrylamide, urea and formaldehyde, phenol and formaldehyde, melamine and formaldehyde, aqueous polyurethane monomers. The monomer has a concentration of 0.1%~30% in the solution or emulsion.

In another preferred embodiment, in step (2), said impregnation step is carried out in vacuum and at a temperature between room temperature to 100° C. for 1 to 48 hours.

In another preferred embodiment, in the step (3), the polymerization of the aqueous polymer monomer is accomplished by heating, light-initiated polymerization, or by spraying an initiator.

In another preferred embodiment, in step (4), said heating is carried out in an inert gas at a temperature of 200 to 800° C. until the polymer was completely carbonized.

In another preferred embodiment, in step (5), said activation step is carried out in an inert gas or a weakly oxidizing gas; said inert gas is nitrogen and said weakly oxidizing gas is carbon dioxide or steam. Said activation temperature is 400 to 1000° C. and the activation time is 0.5 to 24 hours.

In a third aspect of the present invention, there is provided a method to use the catalyst of the present invention to prepare vinyl chloride.

Accordingly, the present invention provided a catalyst for making vinyl chloride that satisfies the requirements of catalytic activity and stability in an industrial process.

DETAILED DESCRIPTION OF THE EMBODIMENT

The present invention provides a catalyst for making vinyl chloride, which comprises: an activated carbon as carrier, a barium compound and a phosphorus compound supported thereon, wherein the barium compound accounts for 0.2% to 20% of the total mass of the catalyst and the phosphorus compound accounts for 0% to 10% of the total mass of the catalyst.

Said barium compound is chosen from barium chloride, etc.

Said phosphorus compound is chosen from phosphoric acid, etc.

The method of preparing a catalyst for making vinyl chloride comprises steps of:

1) mixing a water-soluble barium compound, a water-soluble phosphorus compound, an aqueous polymer monomer with water to make a solution A or an emulsion A;

In step (1), said water-soluble barium compound is chosen from barium chloride, etc., and its aqueous solution has a concentration of 0.3 to 30% (preferably 1 to 20%); said water-soluble phosphorus compound is chosen from phosphoric acid, etc., and its aqueous solution has a concentration of 0 to 10% (preferably 0.5 to 10%); said aqueous polymeric monomer can be a compound capable of polymerizing into a gel that is soluble in water or can form an emulsion in water, wherein said compound is capable of polymerizing into such a gel is chosen from at least one among acrylic compounds, vinyl ester compounds, acrylamide, urea and formaldehyde, phenol and formaldehyde, melamine and formaldehyde, aqueous polyurethane monomers, etc. The concentration of the aqueous polymer monomer in the aqueous solution or the emulsion is 0.1% to 30% (preferably 3~15%). For an aqueous polymeric monomer that is insoluble in water, surfactants can be added to emulsify it to form an emulsion.

2) the activated carbon was added to the solution A or the emulsion A for impregnation;

In step 2), said impregnation is preferably carried out in vacuum so that a solution or emulsion can more fully penetrate into the activated carbon. The impregnation temperature can be between room temperature and 100 °C. (preferably room temperature to 80° C.) and the impregnation time can be 1~48 hours.

3) the activated carbon is removed from the solution, spin-dried, and then let the polymeric monomer polymerize;

In step 3), the polymerization of monomers can be accomplished by heating (e.g. 80 to 100° C.), light initiation (such as ultraviolet radiation), or by spraying an initiator (such as one chosen from ammonium persulfate, sodium bisulfite, and a mixture thereof).

4) heating the activated carbon with the aqueous polymer thereon, drying, and carbonizing the polymer;

In step 4), the heating can be carried out in an inert gas. The heating temperature can be 200 to 800° C. (preferably 300 to 800° C.) until the polymer completely decomposes and is carbonized.

5) activating the carbonized activated carbon and the substance supported thereon and obtaining a catalyst for the preparation of vinyl chloride.

In step 5), the activation can be carried out in an inert gas or a weakly oxidizing gas. Said inert gas can be nitrogen, etc. and said weakly oxidizing gas can be carbon dioxide or steam. Said activation temperature can be 400 to 1000° C. and the activation time can be 0.5~24 hours.

As used herein, "room temperature" and "normal temperature" are used interchangeably, both referring to 10-30 °C., preferably 15-25 °C.

The technical features mentioned above in the present invention, or in the embodiment can be freely combined. All the characteristics disclosed in this specification can be used with any form of a composition. The various features disclosed in the specification can be substituted with any alternatives that can provide the same, equal, or similar purposes. Therefore, unless specified, the features disclosed therein is only general examples among those with equal or similar features.

The main advantage of the present invention is such that compared with the existing catalysts used for the preparation of vinyl chloride and their preparation method, the catalyst preparation method of the present invention provides catalysts with better catalytic activities. The temperature at which the reaction rate can satisfy industrial requirements is decreased from 250 to 320° C. to 180 to 250° C. The catalyst life can be increased from a few hundred hours to several thousand hours. In addition to making vinyl chloride through catalytic reforming of acetylene dichloroethane catalytic reforming of vinyl chloride, this catalyst is suitable for making vinyl chloride through the reaction of acetylene and hydrogen chloride and ammonium chloride, etc.

The present invention is further illustrated using examples below. It should be understood that these embodiments are merely used to illustrate the present invention and not for limiting the scope of the invention. In the following embodiments where experimental conditions have not be specified, the conditions usually are in accordance with the conventional conditions or the conditions recommended by the manufacturer. Unless otherwise specified, all percentages, ratios, proportions, or parts are by weight.

The units in the volume percentage by weight in the present invention are well known to those skilled in the art, for example, the weight of the solute in 100 ml of solution.

Unless otherwise defined, all professional and scientific terms used herein has the same meaning as those skilled in art are familiar with. Furthermore, any similar or equivalent methods and materials can be used in the method of the present invention. The preferred embodiment presented herein are for illustrative purposes only.

EXAMPLE 1

Preparation of Sample 1

1. 5 g of barium chloride, 2 g phosphate, 3 g acid was dissolved in 100 g water to form a solution.

2. 50 g of activated carbon was added into the above solution, preferably under vacuum so that the solution can more fully penetrate into the activated carbon. The temperature of impregnation is 40° C. The duration of the impregnation is 1 hr.

3. The activated carbon was removed from the solution after impregnation and spin-dried using a centrifuge.

4. The spin-dried activated carbon was irradiated with ultraviolet light, initiating polymerization of acrylic acid.

5. The activated carbon supported with an aqueous polymer was heated in an inert gas to remove water and to decompose and carbonize the polymer. The temperature was controlled at 400° C.

6. The activated carbon and substance supported thereon were activated in nitrogen after carbonization. The activation temperature was 1000° C. and the activation time was 0.5 hr.

Sample 1 was obtained after above steps.

EXAMPLE 2

Preparation of Sample 2

1. 10 g of barium chloride, 5 g phosphate, 5 g of vinyl acetate, 0.1 g sodium alkylbenzenesulfonate, and 100 g of water was mixed to form an emulsion.

2. 50 g of activated carbon was added into the above emulsion, preferably under vacuum, so that the emulsion can more fully penetrate into the activated carbon. The impregnation temperature was 60° C. and the impregnation time was 5 hrs.

3. The activated carbon was removed from the solution after impregnation and spin-dried using a centrifuge.

4. 5 g of a solution containing 1% of ammonium persulfate and 1% sodium bisulfite was sprayed onto the activated carbon so that the vinyl acetate polymerization.

5. The activated carbon supported with an aqueous polymer was heated in an inert gas to remove water and to decompose and carbonize the polymer. The temperature was controlled at 500° C.

6. The activated carbon and substance supported thereon were activated in carbon dioxide after carbonization. The activation temperature was 600° C. and the activation time was 2 hr.

Sample 2 was obtained after above-recited steps.

EXAMPLE 3

3 Preparation of Sample 3

1. 15 g of barium chloride, 10 g phosphoric acid, 10 g of acrylamide, were dissolved in 100 g of water to form a solution.

2. 50 g of activated carbon was added into the above solution, preferably under vacuum so that the solution can more fully penetrate into the activated carbon. impregnation temperature was 80° C. and the impregnation time was 10 hrs.

3. The activated carbon was removed from the solution after impregnation and spin-dried using a centrifuge.

4. The activated carbon was radiated using with ultraviolet ray so that the acrylamide monomers polymerized.

5. The activated carbon supported with an aqueous polymer was heated in an inert gas to remove water and to decompose and carbonize the polymer. The temperature was controlled at 600° C.

The activated carbon and substance supported thereon were activated in steam after carbonization. The activation temperature was 700° C. and the activation time was 4 hrs.

Sample 3 was obtained after above-recited steps.

EXAMPLE 4

Preparation of Sample 4

1. 20 g of barium chloride, 5 g of urea, 3 g formaldehyde, and 1 g ammonium chloride were dissolved in 100 g of water to form a solution.

2. 50 g of activated carbon was added into the above solution, preferably under vacuum so that the solution can more fully penetrate into the activated carbon. The impregnation was carried out at room temperature and the impregnation time was 15 hrs.

3. The activated carbon was removed from the solution after impregnation and spin-dried using a centrifuge.

4. The activated carbon was heated to 80° C. after spin-drying so that urea and formaldehyde ploymerized.

5. The activated carbon supported with an aqueous polymer was heated in an inert gas to remove water and to decompose and carbonize the polymer. The temperature was controlled at 300° C.

6. The activated carbon and substance supported thereon were activated in nitrogen after carbonization. The activation temperature was 500° C. and the activation time was 10 hrs.

Sample 4 was obtained after above-recited steps.

EXAMPLE 5

Preparation of Sample 5

1. 20 g of barium chloride, 4 g phosphate, 10 g of phenol, and 5 g formaldehyde were dissolved in 100 g of water to form a solution.

2. 50 g of activated carbon was added into the above solution, preferably under vacuum so that the solution can more fully penetrate into the activated carbon. The impregnation was carried out at room temperature and the impregnation time was 24 hrs.

3. The activated carbon was removed from the solution after impregnation and spin-dried using a centrifuge.

4. The activated carbon was heated to 80° C. so that phenol and formaldehyde polymerized.

5. The activated carbon supported with an aqueous polymer was heated in an inert gas to remove water and to decompose and carbonize the polymer. The temperature was controlled at 650° C.

6. The activated carbon and substance supported thereon were activated in nitrogen after carbonization. The activation temperature was 400° C. and the activation time was 20 hrs.

Sample 5 was obtained after above-recited steps.

EXAMPLE 6

Preparation of sample 6

1. 8 g barium chloride, 1 g phosphate, 2 g melamine, 3 g formaldehyde were dissolved in 100 g of water to form a solution.

2. 50 g of activated carbon was added into the above solution, preferably under vacuum so that the solution can more fully penetrate into the activated carbon. The impregnation was 50° C. and the impregnation time was 48 hrs.

3. The activated carbon was removed from the solution after impregnation and spin-dried using a centrifuge.

4. The activated carbon was heated to 100° C. so that melamine and formaldehyde polymerized.

5. The activated carbon supported with an aqueous polymer was heated in an inert gas to remove water and to decompose and carbonize the polymer. The temperature was controlled at 800° C.

6. The activated carbon and substance supported thereon were activated in nitrogen after carbonization. The activation temperature was 900° C. and the activation time was 24 hrs.

Sample 6 was obtained after above-recited steps.

EXAMPLE 7

Preparation of Sample 7

1. 6 g of barium chloride, 0.5 g phosphate, 3 g of toluene diisocyanate, 3 g glycerol, 0.1 g sodium alkylbenzenesulfonate, and 100 g water forms as an emulsion.

2. 50 g of activated carbon was added to the above emulsion, preferably under vacuum so that the emulsion can fully more penetrate into the activated carbon. The impregnation temperature was 50° C. and the impregnation time was 12 hrs.

3. The activated carbon was removed from the emulsion after impregnation and spin-dried using a centrifuge.

4. The activated carbon was heated to 100° C. after spin-drying so that diisocyanate and glycerin polymerized.

5. The activated carbon supported with an aqueous polymer was heated in an inert gas to remove water and to decompose and carbonize the polymer. The temperature was controlled at 550° C.

6. activated carbon and substance supported thereon were activated in nitrogen after carbonization. The activation temperature was 550° C. and the activation time was 24 hrs.

Sample 7 was obtained after above-recited steps.

COMPARATIVE EXAMPLE

According to the catalyst preparation method disclosed in Chinese patent application 201010149180.1, 5 g of barium chloride were dissolved in 150 ml of water. 100 g of activated carbon was added into the solution, mixing evenly and dried at 150° C. to obtain a catalyst comparative Sample A, which was compared with the above Samples 1-7 in testing. The results are as follows:

1) Comparing catalyst activity: experimental conditions: control pressure of 0.1 MPa, acetylene dichloroethane molar ratio of 1:1, catalyst loading amount of 1000 kg, acetylene flow rate of 800 ml/min. The conversion of acetylene to vinyl chloride measured at various temperatures using different catalysts are shown in Table 1.

TABLE 1

| Sample/ Comparative sample | (%) Temperature (° C.) | | | | | | |
|---|---|---|---|---|---|---|---|
| | 180 | 200 | 220 | 240 | 260 | 280 | 300 |
| Sample 1 | 31.2 | 60.3 | 78.5 | 87.2 | 90.3 | 91.2 | 92.3 |
| Sample 2 | 33.1 | 61.2 | 80.4 | 88.1 | 91.1 | 92.1 | 92.5 |
| Sample 3 | 27.6 | 55.5 | 73.7 | 83.5 | 88.1 | 90.5 | 91.7 |
| Sample 4 | 25.4 | 52.6 | 68.6 | 79.3 | 87.5 | 90.3 | 91.1 |
| Sample 5 | 26.2 | 53.4 | 69.2 | 80.4 | 88.4 | 90.5 | 91.2 |
| Sample 6 | 28.1 | 56.2 | 74.5 | 82.3 | 90.3 | 91.1 | 92.1 |
| Sample 7 | 30.3 | 57.3 | 76.3 | 85.1 | 90.1 | 91.2 | 92.2 |
| Comparative sample A. | 13.2 | 25.8 | 50.4 | 68.3 | 77.5 | 86.3 | 90.49 |

The results show that the low temperature activity of the catalyst prepared by the method of this invention is much higher than the catalyst prepared by the regular impregnation method.

2) Comparing catalyst stability: at the operating temperature of 23° C., a pressure of 0.1 MPa, acetylene to dichloroethane molar ratio of 1:1, catalyst loading amount of 1000 kg, acetylene flow rate of 400 ml/min. The conversion rate from acetylene to vinyl chloride conversion is P. The changes in the conversion rate over time is shown in Table 2.

TABLE 2

| Time (h) | Sample 1 | Sample 2 | Sample 3 | Sample 4 | Sample 5 | Sample 6 | Sample 7 | Comparative sample A. |
|---|---|---|---|---|---|---|---|---|
| 0 | 91.5 | 91.7 | 88.5 | 87.9 | 89.3 | 91.2 | 91.4 | 76.5 |
| 100 | 91.3 | 91.6 | 88.5 | 87.8 | 89.3 | 91.1 | 91.4 | 76.0 |
| 200 | 91.1 | 91.5 | 88.3 | 86.5 | 89.2 | 91.0 | 91.2 | 68.1 |
| 300 | 89.6 | 90.5 | 86.5 | 84.7 | 88.1 | 89.2 | 90.1 | 61.0 |
| 400 | 87.5 | 89.2 | 85.6 | 83.2 | 87.4 | 88.1 | 89.3 | 52.2 |
| 500 | 86.3 | 87.8 | 84.3 | 81.8 | 86.2 | 87.4 | 88.7 | 39.3 |
| 600 | 84.5 | 86.5 | 83.2 | 80.3 | 85.1 | 86.8 | 87.8 | 28.5 |
| 700 | 83.7 | 84.4 | 82.2 | 78.6 | 83.7 | 85.9 | 87.0 | 19.2 |
| 800 | 82.5 | 83.6 | 81.3 | 76.8 | 82.9 | 84.1 | 86.3 | 13.6 |
| 900 | 81.6 | 82.2 | 80.5 | 75.3 | 82.1 | 83.2 | 85.6 | / |
| 1000 | 80.8 | 81.7 | 79.3 | 74.3 | 80.6 | 82.0 | 84.6 | / |
| 1100 | 80.1 | 81.0 | 78.6 | 73.1 | 79.5 | 81.1 | 83.5 | / |
| 1200 | 79.2 | 80.3 | 77.4 | 71.6 | 78.2 | 80.5 | 82.7 | / |
| 1300 | 78.6 | 79.5 | 76.3 | 70.1 | 76.4 | 79.7 | 82.1 | / |
| 1400 | 78.1 | 78.9 | 75.5 | 68.3 | 75.1 | 78.8 | 81.3 | / |
| 1500 | 77.5 | 78.2 | 74.3 | 66.5 | 73.8 | 78.2 | 80.5 | / |

The results show that the catalyst prepared using the method of the present patent application has far better stability than the catalyst prepared by the regular impregnation immersion method.

Described above are preferred embodiments according to the present invention and shall not be used to limited the scope of present invention. The substance of technical content in this invention are generally defined in the claims of the present application. Technologies or methods, if being the same as defined in the claims of the present application or the equivalent thereof, shall be regarded as covered by the claims of the present invention.

What is claimed is:

1. A catalyst for the preparation of vinyl chloride, characterized in that: said catalyst comprises activated carbon as a carrier, a barium compound and a phosphorus compound supported on the carrier, wherein said barium compound has a mass percentage of 0.2% to 20% and said phosphorous compound has a mass percentage of less than 10% based on the total mass of the catalyst,
wherein said phosphorus compound is phosphoric acid.

2. The catalyst of claim 1, wherein said barium compound is barium chloride.

3. A method for preparing a catalyst used in preparing vinyl chloride, comprising the steps of:
   (1) mixing a water-soluble barium compound, a water-soluble phosphorus compound, an aqueous polymer monomer, and water to obtain a solution or an emulsion;
   (2) impregnating the activated carbon in the solution or the emulsion;
   (3) polymerizing the aqueous polymer monomer on the activated carbon after spin-drying to form an aqueous polymer;
   (4) heating the aqueous polymer supported on the activated carbon to form a carbonized polymer;
   (5) activating the activated carbon having the carbonized polymer supported thereon.

4. The preparation method according to claim 3, wherein, in the Step (1), said water-soluble barium compound is barium chloride and a concentration of an aqueous solution of said water-soluble barium compound is 0.3% to 30%; said water-soluble phosphorus compound is phosphoric acid and a concentration of an aqueous solution of a water-soluble compound of the said phosphorus is less than 10%.

5. The preparation method according to claim 3, wherein, in step (1), the aqueous polymer monomer is capable of polymerization into a gel that is water soluble or is capable of forming an emulsion with water, said aqueous polymer monomer is chosen from at least one among acrylic compounds, vinyl ester compounds, acrylamide, a mixture of urea and formaldehyde, a mixture of phenol and formaldehyde, a mixture of melamine and formaldehyde, and aqueous polyurethane monomer, wherein a concentration of the aqueous polymer monomer in the solution or the emulsion is 0.1% to 30%.

6. The method according to claim 3, wherein, in Step (2), said impregnation is carried out under vacuum at a temperature ranging from room temperature to 100° C. for 1 hours to 48 hours.

7. The method according to claim 3, wherein, in Step (3), the aqueous polymer monomer polymerizes using heating, light initiation, or by spraying an initiator.

8. The method according to claim 3, wherein, in Step (4), the heating is carried out in an inert gas at a temperature ranging from 200° C. to 800° C. until the aqueous polymer decomposes and carbonizes.

9. The method according to claim 3, wherein, in Step (5), the activation is carried out in an inert gas or a weakly oxidizing gas, wherein said inert gas is nitrogen and said weak oxidizing gas is carbon dioxide or steam, wherein said activation temperature ranges from 400° C. to 1000° C. and said activation time ranges from 0.5 hours to 24 hours.

10. A method of preparing vinyl chloride, comprising the step of:
   obtaining a catalyst;
   reacting acetylene and dichloroethane in the presence of said catalyst,
   wherein said catalyst comprises activated carbon as a carrier, a barium compound and a phosphorus compound supported on the carrier, wherein said barium compound has a mass percentage of 0.2% to 20% and said phosphorous compound has a mass percentage of less than 10% based on the total mass of the catalyst,
   wherein said phosphorus compound is phosphoric acid.

11. The method of preparing vinyl chloride of claim 10, wherein said barium compound is barium chloride.

* * * * *